(12) United States Patent
Bethune et al.

(10) Patent No.: US 7,575,906 B2
(45) Date of Patent: Aug. 18, 2009

(54) CATALASE DECOMPOSITION OF HYDROGEN PEROXIDE IN SURFACTANTS

(75) Inventors: Kristie Joyce Bethune, Maineville, OH (US); Terry Franklin Formyduval, Cincinnati, OH (US); Jared John Schaefer, Cincinnati, OH (US); Manuel Venegas, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/074,598

(22) Filed: Mar. 5, 2008

(65) Prior Publication Data
US 2008/0220496 A1 Sep. 11, 2008

Related U.S. Application Data

(60) Provisional application No. 60/904,950, filed on Mar. 5, 2007.

(51) Int. Cl.
*C12P 13/00* (2006.01)
*C12N 9/02* (2006.01)
*C12N 9/08* (2006.01)

(52) U.S. Cl. .................. 435/128; 435/174; 435/189; 435/192

(58) Field of Classification Search .................. None
See application file for complete search history.

(56) References Cited

U.S. PATENT DOCUMENTS

| | | | |
|---|---|---|---|
| 5,409,532 A | | 4/1995 | Astegger et al. |
| 5,891,370 A | * | 4/1999 | Connor et al. ............. 264/37.2 |
| 6,007,727 A | | 12/1999 | Bohrer et al. |
| 6,503,876 B1 | * | 1/2003 | Broeckx ..................... 510/349 |
| 6,699,828 B1 | * | 3/2004 | de Buzzaccarini et al. .. 510/372 |
| 6,726,362 B1 | * | 4/2004 | Frisch et al. ................ 383/103 |
| 2001/0041188 A1 | | 11/2001 | Gibbins et al. |
| 2003/0224054 A1 | | 12/2003 | Gibbins et al. |
| 2004/0147423 A1 | | 7/2004 | Scialla et al. |
| 2006/0182653 A1 | * | 8/2006 | Sizer .......................... 422/28 |

FOREIGN PATENT DOCUMENTS

| | | |
|---|---|---|
| CA | 1991/2016321AA | 11/1991 |
| EP | 0 866 058 A2 | 9/1998 |
| EP | 0 866 058 A3 | 8/2002 |
| JP | 08-141578 A2 | 6/1996 |
| JP | 11-092443 A2 | 4/1999 |
| JP | 2005-235437 A | 9/2005 |
| WO | WO 01/00765 A1 | 1/2001 |
| WO | WO 01/49258 A2 | 7/2001 |

OTHER PUBLICATIONS

PCT International Search Report, Mailed Jul. 22, 2008, 3pgs, International Application No. PCT/IB2008/050782.
Costa, Silgia A., et al, Immobilization of catalases from Bacillus SF on alumina for the treatment of textile bleaching effluents, Enzyme and Microbial Technology, 2001, pp. 815-819, vol. 28.
Genencor International, Catalase T100, Product Specification Sheet, Mar. 2, 1998.
Genencor International, Oxy-Gone T400, Product Specification Sheet, Apr. 15, 2005.
Poduslo, Joseph F., et al., Therapeutic Benefit of Polyamine-Modified Catalase as a Scavenger of Hydrogen Peroxide and Nitric Oxide in Familial Amyotrophic Lateral Sclerosis Transgenics, Annals of Neurology, 2000, pp. 943-947, vol. 48, No. 6.
Akaike, Takaaki, et al., Bactericidal Activity of Alkyl Peroxyl Radicals Generated by Heme-Iron-Catalyzed Decomposition of Organic Peroxides, Archives of Biochemistry and Biophysics, 1992, pp. 55-63, vol. 294, No. 1.
Wykretowicz, A., et al., Dipyridamole Inhibits Hydroxylamine Augmented Nitric Oxide (NO) Production by Activated Polymorphonuclear Neutrophils Through an Adenosine-Independent Mechanism, Physiological Research, 2004, pp. 645-652, vol. 53.
Konoplina, A. A., et al., Activating Effect Of Organic Compounds On The Catalase Activity Of Lead Oxide, Russian Journal Of Physical Chemistry, Dec. 1967, pp. 1687-1689, vol. 41, No. 12.
Inagaki, M., Zinc Oxide Enhancement of the Chemiluminescence by Rat Neutrophils: Etiological Studies in Zinc Fume Fever, Journal of the Juzen Medical Society, 1999, pp. 273-282, vol. 108, No. 2.
Wieland, Heinrich, Mechanism of Oxidation Processes, Berichte der Deutschen Chemischen Gesellschaft {Abteilung} B: Abhandlungen, 1921, pp. 2353-2376, vol. 54B.
Bernard, M. Michel L. J., Polarographic Study of the Catalase and Peroxidase Reactions of Hydrogen Peroxide and Organic Peroxides, Compt. Rend. (1954), vol. 239, pp. 1248-1250.

* cited by examiner

*Primary Examiner*—Herbert J. Lilling
(74) *Attorney, Agent, or Firm*—Nicole M. Tepe; Kim William Zerby; Steven W. Miller

(57) ABSTRACT

A process comprising the steps of continuously adding a catalase enzyme to a process stream, wherein the process stream comprises an amine oxide surfactant and hydrogen peroxide; and mixing the process stream and catalase enzyme.

21 Claims, 3 Drawing Sheets
(2 of 3 Drawing Sheet(s) Filed in Color)

CATALASE DECOMPOSITION OF HYDROGEN PEROXIDE IN SURFACTANTS

CROSS-REFERENCE TO RELATED APPLICATION

This application claims priority under 35 U.S.C. § 119(e) to U.S. Provisional Application Ser. No. 60/904,950 filed Mar. 5, 2007.

FIELD OF THE INVENTION

The present invention relates to a process for preparing long chain amine oxide surfactants. The process comprises decomposing a portion of the excess hydrogen peroxide added into the process to form the amine oxide with a catalase.

BACKGROUND OF THE INVENTION

Long chain amine oxide surfactants produce rich stable foams in water and have properties that result in a high degree of grease cutting. Therefore, amine oxide surfactants are frequently chosen as a component of hand dishwashing liquids, cleansers, and other products where foaming is desirable. Amine oxides are also capable of being successfully used in chlorine/bleach products where other surfactants may not be acceptable.

Long chain amine oxide surfactants may be prepared by the oxidation of tertiary amines. Long chain amine oxides may be produced in a process comprising oxidizing a tertiary amine with hydrogen peroxide. In such reactions, hydrogen peroxide in added to the process in a stoichiometric excess to ensure that predominantly all the tertiary amine is converted to amine oxide. The oxidation reaction is typically conducted at a temperature in the range of from about 60° to about 100° C. After conversion of the tertiary amine to amine oxide, there remains excess hydrogen peroxide in the process stream containing the amine oxide. The presence of even relatively small amounts of excess hydrogen peroxide (i.e. in excess of 100 ppm) in amine oxides used in formulation of liquid detergents can result in skin irritation and odor problems. The odor problems are especially evident in liquid detergents that are formulated with diamine compounds such as diaminopentane, a pH buffer that may be used in detergents.

Conventional processes rely on simple decomposition of the excess hydrogen peroxide to eliminate the hydrogen peroxide from the product stream. The decomposition is achieved by maintaining the product stream comprising the amine oxide at high temperatures for a sufficient time. Unfortunately, high temperature thermal decomposition of the hydrogen peroxide results in formation of unwanted byproducts in the amine oxide surfactant. In certain applications, if the high temperature hydrogen peroxide decomposition is continued to a point where the hydrogen peroxide is totally removed from the amine oxide surfactant, other concerns such as color stability and other odor problems may occur.

Therefore, there is a need for a process to more efficiently remove the hydrogen peroxide from a product process stream comprising long chain amine oxides. More specifically, there is a need for a process that can decompose the hydrogen peroxide from a process stream comprising long chain amine oxides to a concentration of less than 100 ppm, as well as reducing the formation of byproducts formed by excess heating of the process stream.

SUMMARY OF THE INVENTION

Embodiments of the process of the invention are directed to a process comprising the steps of adding a catalase enzyme to a process stream, wherein the process stream comprises an amine oxide surfactant and hydrogen peroxide. The catalase may be added continuously, intermittently, or in a batch. The concentration of catalase in the process stream based upon activity may be in the range of greater than about 2000 U/mol of hydrogen peroxide to less than about 15,000 U/mol of hydrogen peroxide.

In another embodiment, the process comprises the steps of reacting a long chain fatty tertiary amine with an excess of hydrogen peroxide to obtain a process stream comprising fatty tertiary amine oxide and unreacted hydrogen peroxide and contacting a catalase enzyme to the process stream to catalyze decomposition of the unreacted hydrogen peroxide, wherein the concentration of catalase is greater than 0 and less than about 1 U/gram of amine oxide. In such embodiments, the catalase may decompose the hydrogen peroxide to within a range of greater than about 20 ppm to less than about 500 ppm in the process stream.

It should be noted that, as used in this specification and the appended claims, the singular forms "a," "and," and "the" include plural referents unless the context clearly dictates otherwise. Thus, for example, reference to "a polymer" may include more than one polymer.

Unless otherwise indicated, all numbers expressing quantities of ingredients, time, temperatures, and so forth used in the present specification and claims are to be understood as being modified in all instances by the term "about." Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may inherently contain certain errors necessarily resulting from the standard deviation found in their respective testing measurements.

It is to be understood that this invention is not limited to specific compositions, components or process steps disclosed herein, as such may vary. It is also to be understood that the terminology used herein is for the purpose of describing particular embodiments only, and is not intended to be limiting.

BRIEF DESCRIPTION OF THE FIGURES

The patent or application file contains at least one drawing executed in color. Copies of this patent or patent application publication with color drawing(s) will be provided by the Office upon request and payment of the necessary fee.

Features and advantages of certain non-limiting embodiments of the alloys, articles and methods described herein may be better understood by reference to the accompanying drawings in which.

Figure 1:
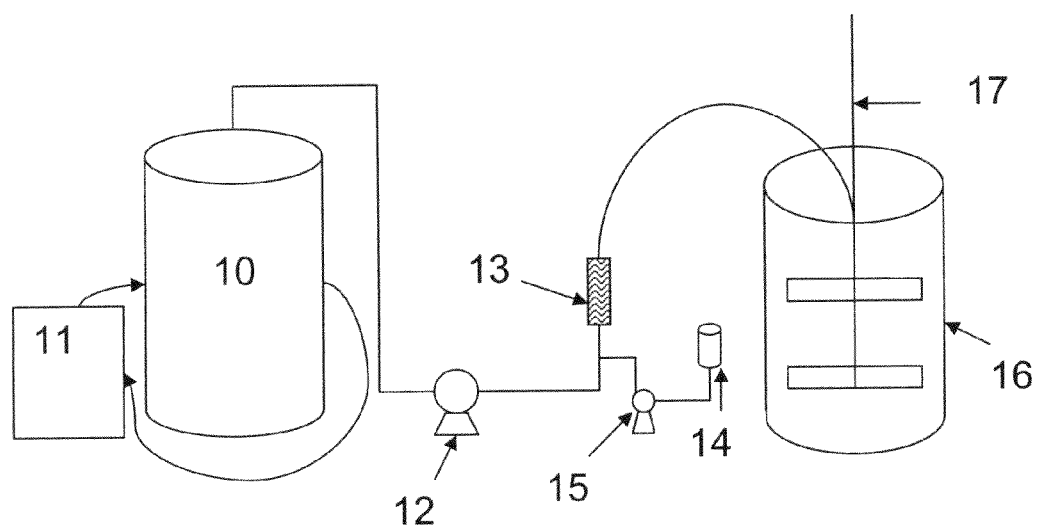
FIG. 1 is a simplified flow diagram of embodiments of the process comprising continuously adding a catalase enzyme to a process stream, wherein the process stream comprises an amine oxide surfactant and hydrogen peroxide.

The reader will appreciate the foregoing details, as well as others, upon considering the following detailed description of certain non-limiting embodiments of process for decomposition of hydrogen peroxide. The reader also may comprehend certain of such additional details upon carrying out or using the alloys, articles and methods described herein.

DETAILED DESCRIPTION OF THE INVENTION

Embodiments of the present invention are directed toward a process for the decomposition of hydrogen peroxide in an aqueous solution comprising a long chain amine oxide surfactant. Embodiments of the process of the invention comprise adding a catalase enzyme, or simply a catalase, to a reaction medium. The reaction medium comprises a long chain amine oxide surfactant and hydrogen peroxide.

Hydrogen peroxide is a strong oxidizer and may be used to oxidize tertiary amines to amine oxides, as in the production of long chain amine oxide surfactants. Though the reaction of hydrogen peroxide with a tertiary amine is presently the most commercially significant process, hydrogen peroxide may also be used to oxidize primary and secondary amines. The oxidation reaction for tertiary amines follows the equation in Reaction Scheme 1. The reaction to form amine oxides is an exothermic, second order reaction between the tertiary amine and hydrogen peroxide.

Reaction Scheme 1: Oxidation of tertiary amines to amine oxides

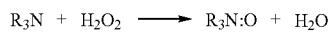

$$R_3N + H_2O_2 \longrightarrow R_3N{:}O + H_2O$$

The tertiary amine to be oxidized may be aliphatic, aromatic, heterocyclic, alicyclic, or a combination thereof. For example in some embodiments, the amine oxide surfactants are prepared from the long chain fatty tertiary amines selected from the group consisting of trioctylamine, tridecylamine, tridodecylamine, didodecylmethylamine, ditetradecylmethylamine, dihexadecylmethylamine, dioctadecylmethylamine, decyldimethylamine, dodecyldimethylamine, tetradecyldimethylamine, hexadecyldimethylamine, octadecyldimethylamine, $C_{12}$-$C_{18}$ alkyldimethyl amines, and mixtures thereof. The degree of conversion of tertiary amines to its amine oxide in commercial processes typically ranges from about 85 wt. % to 99.5 wt. % depending on the purity of the long chain tertiary amine and the amount of excess hydrogen peroxide added to the reaction medium. The process is typically carried out at a pH in the range of from about 7 to about 10, more typically from about 8 to about 10.

In order to drive the reaction forward, toward the formation of the amine oxide, excess hydrogen peroxide may be added to the reaction medium. It should be noted that the oxidation step may also be performed by adding a source of hydrogen peroxide, by generating hydrogen peroxide in situ. For use in the process, hydrogen peroxide is commercially available in aqueous solutions of various strengths up to 90%. The hydrogen peroxide is typically added as an aqueous solution comprising hydrogen peroxide in a concentration of 5 wt. % to 70 wt. % in water. To simplify the process, the concentration of the hydrogen peroxide may be chosen such that the desired concentration of amine oxide surfactant is formed in the reaction medium with no further addition or removal of water.

Certain embodiments of the process of the present invention, however, may comprise adjusting the concentration of the amine oxide product with a solvent, such as water. The amount of aqueous hydrogen peroxide added to the amine will be such that the reaction medium comprises at least a stoichiometric amount of hydrogen peroxide based upon amine, but typically will comprise a stoichiometric excess of hydrogen peroxide of about 1 mol. % to about 20 mol. %, or more specifically, about 1 mol. % to 10 mol. %.

The reaction temperature of the oxidation of the amines may be from about 40° C. to about 100° C. Preferably, the reaction temperature is maintained in the range of from about 60° C. to about 70° C. in an attempt to limit the formation of byproducts in the product surfactant. The reaction may be monitored to determine when the conversion of amine to amine oxide has reached greater than about 90%, or in certain embodiments greater than about 95%. When conversion of the amine to amine oxide has reached the desired levels, the residual hydrogen peroxide is still typically in a concentration in the range of from about 1500 to about 3000 ppm. At this point in the prior art processes, the reaction medium was maintained at such a temperature until the residual hydrogen peroxide was thermally decomposed to a level of less than 50 ppm. The decomposition reaction is time consuming and maintaining the reaction medium at an elevated temperature for this extended period of time resulted in the production of byproducts resulting in discoloration of the product.

Embodiments of the process of the present invention comprise continuously adding a catalase enzyme to a process stream, wherein the process stream comprises an amine oxide surfactant and hydrogen peroxide and mixing the process stream and the catalase enzyme. Catalase is a common enzyme found in living organisms. In nature, the presence of catalase reduces the harmful effect of the presence of hydrogen peroxide in the cell. Catalases from different organic sources also have different activities. Catalases are also used commercially to catalyze the decomposition of hydrogen peroxide to water and oxygen. It is important to note that catalase has one of the highest turnover rates for all enzymes, under optimal conditions, one mole of catalase can decompose over 500 million moles of hydrogen peroxide to water and oxygen per second. The decomposition reaction follows first-order kinetics within short reaction times (<3 min) at relatively high enzyme concentrations. In addition to the mechanism described above, catalase is gradually, irreversibly oxidized by hydrogen peroxide; so long reaction periods or dilute solutions of enzyme result in deviation from first-order behavior.

Further, the activity of a catalase is influenced by several factors including, but not limited to, the concentration of hydrogen peroxide, temperature, pH, and the presence of inhibitors or activators. Enzymatic activity, typically indicated as U/gram, decreases when an enzyme is exposed to conditions that are outside the optimal range. For example, the rate of the enzymatic decomposition reaction of hydrogen peroxide in the presence of catalase decreases with decreasing concentrations of hydrogen peroxide. However, at higher concentrations, the maximum rate for the decomposition reaction will be achieved and further increases in hydrogen peroxide concentration will have no effect.

Enzyme catalyzed reactions also tend to increase in rate as the temperature increases, that is until an optimal temperature is reached. Above the optimal temperature, the activity of the enzyme decreases and temperatures above about 40° C. to about 50° C. denature many enzymes, such as catalase.

pH also affects the activity of a catalase. The reaction medium comprising the amine oxides and the hydrogen peroxide is typically at a pH in the range of from about 7 to about 10, more preferably from about 8 to about 10. In the basic pH range, greater than 7, the catalase tends to lose hydrogen ions to the reaction medium, thus changing its conformation and decreasing enzymatic activity. The presence of surfactants has been shown to inhibit enzymatic activity of catalase in certain cases.

Although catalase activity is so high, the inventors have surprisingly found that the degree of decomposition of the hydrogen peroxide in the process for preparation of amine oxide surfactants may be controlled using a catalase. The inventors have determined that under certain conditions a desired concentration of residual hydrogen peroxide may remain in the process stream comprising the amine oxide surfactant. All of the inhibition effects may be utilized to result in the desired degree of decomposition. In embodiments of the process of the invention it is not desirable to remove all the hydrogen peroxide from the reaction medium comprising the amine oxide surfactant. A residual amount of hydrogen peroxide in the process stream comprising the amine oxide surfactant will help maintain the color of the surfactant, reduce microbial activity in the surfactant, and prevent generation of odors from the surfactant. However, the high concentration of hydrogen peroxide may cause skin irritation in certain applications of the surfactant. Therefore, embodiments of the process of the invention comprise decomposing the hydrogen peroxide to a concentration greater than zero but less than about 1000 ppm. Further embodiments comprise decomposing the hydrogen peroxide to a concentration greater than about 20 ppm but less than about 500 ppm and, in other embodiments, the residual hydrogen peroxide may be present in a concentration from about 20 ppm to about 200 ppm, or even from about 20 ppm to about 100 ppm.

The inventors have found that the degree of decomposition of the hydrogen peroxide may be controlled by several factors, including adding a certain activity of catalase based upon the amount of excess hydrogen peroxide in the reaction medium after completion of conversion of amine to amine oxide, the temperature of the reaction medium, the pH, and decomposition time. Therefore, embodiments of the process of the present invention comprise adding a catalase enzyme to a process stream to obtain a concentration of catalase based upon activity that is greater than about 2000 U/mol of hydrogen peroxide to less than about 8000 U/mol of hydrogen peroxide, or in some embodiments, the concentration of catalase based upon activity that is greater than about 2000 U/mol of hydrogen peroxide to less than about 4000 U/mol of hydrogen peroxide. The actual amount of catalase added depends on the activity of the specific catalase used in the reaction. Commercially available catalases have a wide range of activity, expressed as a range of U/gram of catalase.

Table 1 includes experiments where process conditions are modified to determine conditions that result in an amount of residual hydrogen peroxide. The experimental reaction system comprising a semi-continuous hydrogen peroxide decomposition by catalase as shown in FIG. 1 as a simplified flow diagram may be used to determine the residual hydrogen peroxide concentration under various conditions.

An aqueous solution comprising an amine oxide surfactant and excess hydrogen peroxide is prepared and stored in amine oxide feed tank 10. The temperature of the process medium in amine oxide feed tank 10 is maintained at a desired temperature by a heat exchanger 11. In the Examples the temperature of the aqueous solution in amine oxide feed tank 10 is maintained in a range from about 45° C. to about 60° C. to mimic the commercial process as closely as possible. Feed pump 12 transfers the aqueous solution from amine oxide feed tank 10 through static mixer 13 and into treated amine oxide collection tank 16. Catalase enzyme is stored in catalase feed tank 14 and transferred into the aqueous solution prior to the static mixer 13. The catalase decomposes the excess hydrogen peroxide in the aqueous solution and the treated amine oxide solution is continuously stirred by agitator 17 in the treated amine oxide collection tank 16.

EXAMPLES

The example processes are conducted using equipment as shown in the simplified flow diagram of FIG. 1. The aqueous solution is transferred from the amine oxide storage tank 10 at approximately 5 gallons/minute. The concentration of amine oxide surfactant in the aqueous solution is constant at approximately 32 wt. % for each experiment. Samples are taken and residual peroxide analyzed from the treated amine oxide collection tank 16. Samples are withdrawn from the collection tank 16 at various times shown in Table 1 for Runs #1 to #5 after the transfer of aqueous solution from the amine oxide feed tank 10 was stopped. Additional samples are withdrawn over time (up to 9 weeks, see FIG. 3) to determine effect of 'aging' on hydrogen peroxide decomposition after treatment with catalase. Though all the experiments are shown here in a continuous process, the process of the invention may also be conducted in a batch process, for example, a process comprising adding a catalase enzyme to a storage or reaction vessel, wherein the vessel comprises an amine oxide surfactant and hydrogen peroxide. All other features of the invention described herein would also apply to the batch process.

In Runs #1 and #2, the catalase is added to the reaction medium to a concentration of 386 U/mol and 1203 U/mol. Surprisingly, this resulted in much less decomposition of hydrogen peroxide than was expected due to the reported activities for catalase decomposition. The combined inhibiting effects of the process stream quickly reduced the activity of the catalase.

TABLE 1

Excess Hydrogen Peroxide Decomposition by Catalase Addition

| | Temp °C. | time (min) | Peroxide (ppm) | [$H_2O_2$] ($\mu$mol/gAO) | Activity (U/mol $H_2O_2$) | $\Delta$ [$H_2O_2$] ([$H_2O_2$]-[$H_2O_2$]$_o$) |
|---|---|---|---|---|---|---|
| Run #1: Catalase Concentration 0.31 ppm | | | | | | |
| Activity (U/gAO) | | | | | | |
| 0.026 | 50 | 0 | 2287.00 | 67.26 | 386.53 | 0 |
| 0.026 | | 5 | 2056.64 | 60.49 | | 6.78 |

TABLE 1-continued

Excess Hydrogen Peroxide Decomposition by Catalase Addition

| Activity (U/g) | Temp °C. | time (min) | Peroxide (ppm) | [$H_2O_2$] ($\mu$mol/gAO) | Activity (U/mol $H_2O_2$) | $\Delta$ [$H_2O_2$] ([$H_2O_2$]-[$H_2O_2$]$_o$) |
|---|---|---|---|---|---|---|
| 0.026 | | 15 | 1440.08 | 42.36 | | 24.91 |
| 0.026 | | 25 | 1451.80 | 42.70 | | 24.56 |
| 0.026 | | 32 | 1466.27 | 43.13 | | 24.14 |
| 0.026 | | 60 | 1515.19 | 44.56 | | 22.70 |
| 0.026 | | 1250 | 1518.46 | 44.66 | | 22.60 |
| Run #2: Catalase Concentration 0.76 ppm | | | | | | |
| 0.064 | 60 | 0 | 1808.47 | 53.19 | 1203.22 | 0 |
| 0.064 | | 5 | 1414.69 | 41.61 | | 11.58 |
| 0.064 | | 15 | 1390.14 | 40.89 | | 12.30 |
| 0.064 | | 25 | 1403.98 | 41.29 | | 11.90 |
| 0.064 | | 40 | 1371.84 | 40.35 | | 12.84 |
| 0.064 | | 90 | 1375.95 | 40.47 | | 12.72 |
| 0.064 | | 1150 | 1391.53 | 40.93 | | 12.26 |
| Run #3: Catalase Concentration 6.95 ppm | | | | | | |
| 0.97 | 54 | 0 | 2411.86 | 70.94 | 13674.07 | 0 |
| 0.97 | | 5 | 130.77 | 3.85 | | 67.09 |
| 0.97 | | 15 | 69.28 | 2.04 | | 68.90 |
| 0.97 | | 25 | 71.26 | 2.10 | | 68.84 |
| 0.97 | | 45 | 53.68 | 1.58 | | 69.36 |
| 0.97 | | 120 | 61.88 | 1.82 | | 69.12 |
| 0.97 | | 240 | 76.72 | 2.26 | | 68.68 |
| 0.97 | | 1335 | 55.69 | 1.64 | | 69.30 |
| Run #4: Catalase Concentration 1.87 ppm | | | | | | |
| 0.26 | 42 | 0 | 2237.29 | 65.80 | 3951.21 | 0 |
| 0.26 | | 5 | 380.42 | 11.19 | | 54.61 |
| 0.26 | | 15 | 92.94 | 2.73 | | 63.07 |
| 0.26 | | 25 | 67.92 | 2.00 | | 63.80 |
| 0.26 | | 40 | 82.18 | 2.42 | | 63.39 |
| 0.26 | | 60 | 69.33 | 2.04 | | 63.76 |
| 0.26 | | 170 | 59.77 | 1.76 | | 64.04 |
| 0.26 | | 1330 | 43.42 | 1.28 | | 64.53 |
| Run #5: Catalase Concentration 1.74 ppm | | | | | | |
| 0.24 | 52 | 0 | 2092.31 | 61.54 | 3900.00 | 0 |
| 0.24 | | 5 | 697.00 | 20.50 | | 41.04 |
| 0.24 | | 15 | 310.26 | 9.13 | | 52.41 |
| 0.24 | | 25 | 290.92 | 8.56 | | 52.98 |
| 0.24 | | 45 | 308.35 | 9.07 | | 52.47 |
| 0.24 | | 60 | 267.13 | 7.86 | | 53.68 |
| 0.24 | | 145 | 266.24 | 7.83 | | 53.71 |
| 0.24 | | 280 | 267.13 | 7.86 | | 53.68 |

In Run #3, the activity of the catalase added is increased. The concentration of hydrogen peroxide in the amine oxide surfactant process stream drops quickly (within 5-15 minutes) to the desired concentration. Surprisingly, after the initial 15 minutes of decomposition, further decomposition does not significantly occur and the concentration of hydrogen peroxide is stable for over twenty hours.

In Runs #4 and #5, the catalase is continuously added to the process stream comprising the amine oxide surfactant and the excess hydrogen peroxide at a concentration of about 3900 U/mol of hydrogen peroxide. In experiment #4, the initial temperature of process stream is 42° C. and after 1330 minutes the peroxide is reduced to 43 ppm. While in experiment #5, the initial temperature is 52° C. and after 60 minutes the concentration of hydrogen peroxide is stabilized at about 270 ppm.

Figure 2:
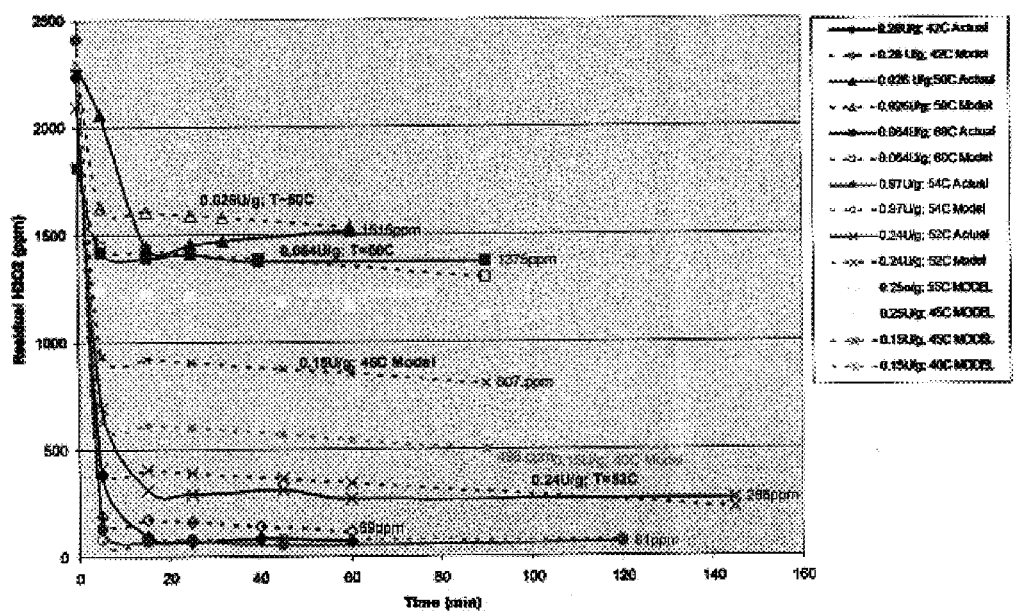
FIG. 2 is a graph showing the concentration of residual hydrogen peroxide after exposure to a catalase enzyme according to embodiments of the present invention.

The graph of FIG. 2 shows the change in hydrogen peroxide levels with time for various combinations of catalase activity per mol of hydrogen peroxide or gram of amine oxide and initial temperature. The graph clearly shows the rapid decomposition of the hydrogen peroxide within the first 10 to 20 minutes. After the rapid decomposition, the residual concentration of hydrogen peroxide stabilizes and surprisingly no further significant decomposition occurs. Such a decomposition curve is unexpected and desired for amine oxide surfactant processing. It is a surprising result that a catalase did not completely decompose the residual hydrogen peroxide at the concentrations added. Such a result would be expected since catalases are such highly active enzymes and rapid decomposition of all the hydrogen peroxide would be expected to occur resulting in color, odor, and microbial activity problems in the product. However, the inventors have found that due to the pH, temperature control and proper catalase selection, the desired concentrations of residual hydrogen peroxide may be obtained.

A mathematical model of the decomposition of hydrogen peroxide by continuously adding a catalase enzyme to a process stream, wherein the process stream comprises an amine oxide surfactant and hydrogen peroxide may be prepared. The graph of FIG. 2 also includes lines indicating the output data from such a model. As can be seen from FIG. 2, the output of the mathematical model closely matches the data obtained from actual examples. The results of the mathematic model of such a system are shown in dashed lines.

Figure 3:
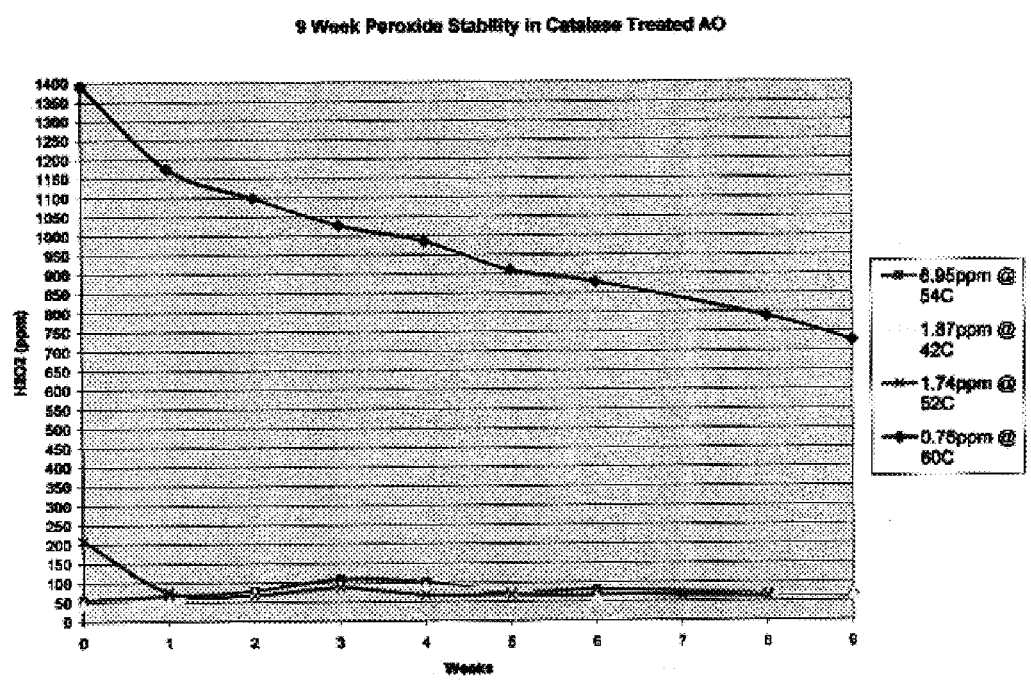
FIG. 3 is a graph of the results of the long term stability tests or aging tests showing the concentration of hydrogen peroxide in the amine oxide surfactant for a period of nine weeks after the initial addition of catalase.

Due to the desirability of maintaining a certain concentration of hydrogen peroxide in the amine oxide surfactant, the samples produced in Runs #1 through #5 are maintained and tested weekly to determine residual hydrogen peroxide concentration. FIG. 3 is a graph of the long term stability tests or aging tests showing the concentration of hydrogen peroxide in the amine oxide surfactant for a period of nine weeks after the initial addition of catalase. Though all samples show stability of hydrogen peroxide concentration, Runs #2 to #5 show the most stability. As can be clearly seen in FIG. 3, the residual hydrogen concentration is maintained within a narrow range for the entire nine week test period.

Although the foregoing description has necessarily presented only a limited number of embodiments, those of ordinary skill in the relevant art will appreciate that various changes in the details of the examples that have been described and illustrated herein may be made by those skilled in the art, and all such modifications will remain within the principle and scope of the present disclosure as expressed herein and in the appended claims. It will also be appreciated by those skilled in the art that changes could be made to the embodiments above without departing from the broad inventive concept thereof. It is understood, therefore, that this invention is not limited to the particular embodiments disclosed herein, but it is intended to cover modifications that are within the principle and scope of the invention, as defined by the claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for limiting hydrogen peroxide concentration in a composition, comprising the steps of:
    a) providing a process stream comprising an amine oxide surfactant and hydrogen peroxide, wherein the concentration of hydrogen peroxide in the stream is greater than about 2000 ppm;
    b) continuously adding a catalase to the process stream; and
    c) reacting the process stream with a catalase wherein the final concentration of the hydrogen peroxide in the composition is in the range of greater than about 20 ppm to less than about 500 ppm and the temperature for the reaction is maintained between from about 40° C. to about 65° C.

2. The process of claim 1, wherein the concentration of catalase based upon activity is greater than about 2000 U/mol of hydrogen peroxide to less than about 8000 U/mol of hydrogen peroxide.

3. The process of claim 1, wherein the catalase is a liquid.

4. The process of claim 1, wherein the concentration of hydrogen peroxide in the process stream is greater than 2000 ppm before addition of the catalase.

5. The process of claim 1, wherein the process stream comprises from about 25 wt % to about 40 wt % of the amine oxide surfactant and greater than 2000 ppm of hydrogen peroxide before addition of the catalase.

6. The process of claim 1, wherein the process stream is at a temperature between about 40° C. and about 65° C.

7. The process of claim 6, wherein the process stream is at a temperature between about 45° C. and about 60° C.

8. The process of claim 1, wherein the mixing comprises at least one of flowing the process stream through an inline mixer, mixing in a stuffed tank, or mixing by turbulence in piping.

9. The process of claim 1, further comprising the step of:
    d) adjusting the temperature of the process stream to maintain a temperature between about 40° C. and about 65° C.

10. The process of claim 1, wherein the concentration of hydrogen peroxide in the process stream is reduced to less than about 500 ppm and greater than about 20 ppm.

11. The process of claim 1, wherein the concentration of hydrogen peroxide in the process stream is reduced to less than about 100 ppm and greater than about 20 ppm.

12. A process for limiting hydrogen peroxide concentration in a composition comprising the steps of:
    a) reacting a long chain fatty tertiary amine with an excess of hydrogen peroxide to obtain a process stream comprising fatty tertiary amine oxide and unreacted hydrogen peroxide, wherein the concentration of hydrogen peroxide in the stream is greater than about 2000 ppm ; and
    b) contacting the process stream to a catalase to catalyze decomposition of the unreacted hydrogen peroxide, wherein the concentration of catalase is greater than 0 and less than about 1 U/gram of amine oxide wherein the final concentration of the hydrogen peroxide in the composition is in the range of greater than about 20 ppm to less than about 500 ppm and the temperature for the reaction is maintained between from about 40° C. to about 65° C.

13. The process of claim 12, wherein the long chain fatty tertiary amine is selected from the group consisting of trioctylamine, tridecylamine, tridodecylamine, didodecylmethylamine ditetradecylmethylamine, dihexadecylmethylamine, dioctadecylmethylamine, decyldimethylamine, dodecyldimethylamine, tetradecyldimethylamine, hexadecyldimethylamine, octadecyldimethylamine, and mixtures thereof.

14. The process of claim 12, wherein the catalase decomposed the hydrogen peroxide to less than about 500 ppm in the process stream.

15. The process of claim 14, wherein the catalase decomposed the hydrogen peroxide to less than about 500 ppm in the process stream and greater than about 20 ppm.

16. The process of claim 14, wherein the concentration of hydrogen peroxide in the process stream is reduced to less than about 100 ppm and greater than about 20 ppm.

17. The process of claim 12, wherein the decomposition is continued until the hydrogen peroxide is less than about 1 wt % of the original level of hydrogen peroxide.

18. The process of claim 17, wherein the decomposition is continued until the hydrogen peroxide is less than about 0.1 wt % of the original level of hydrogen peroxide.

19. The process of claim 12, additionally comprising the step of:
   c) cooling the process stream to maintain a temperature between about 40° C. and about 65° C.

20. The process of claim 12, wherein the contacting of the process stream is the continuous addition of the catalase to the process stream.

21. The process of claim 12, wherein the contacting of the process stream comprises passing the process stream over a bed of immobilized catalase.

* * * * *

UNITED STATES PATENT AND TRADEMARK OFFICE
CERTIFICATE OF CORRECTION

PATENT NO. : 7,575,906 B2  Page 1 of 1
APPLICATION NO. : 12/074598
DATED : August 18, 2009
INVENTOR(S) : Kristie Joyce Bethune et al.

It is certified that error appears in the above-identified patent and that said Letters Patent is hereby corrected as shown below:

Column 2
Before line 53, insert -- The patent or application file contains at least one drawing executed in color. Copies of this patent or patent application publication with color drawing(s) will be provided by the Office upon request and payment of the necessary fee. --.

Claim 8
Line 3, delete "stuffed" and insert -- stirred --.

Signed and Sealed this

Thirty-first Day of August, 2010

David J. Kappos
*Director of the United States Patent and Trademark Office*